US 6,555,360 B1

(12) United States Patent
Srienc et al.

(10) Patent No.: US 6,555,360 B1
(45) Date of Patent: Apr. 29, 2003

(54) FLOW INJECTION FLOW CYTOMETRY SYSTEM FOR ON-LINE MONITORING OF BIROREACTORS AND METHOD FOR MONITORING

(76) Inventors: Friedrich Srienc, 4955 Jerome Ave. North, Lake Elmo, MN (US) 55042; Rui Zhao, 1130 Indian Autumn Trace, Houston, TX (US) 77062; Arvind Natarajan, 204 Brunswick Ct., Lansdale, PA (US) 19446

( * ) Notice: Subject to any disclaimer, the term of this patent is extended or adjusted under 35 U.S.C. 154(b) by 0 days.

(21) Appl. No.: 09/280,757

(22) Filed: Mar. 29, 1999

Related U.S. Application Data

(60) Provisional application No. 60/079,970, filed on Mar. 30, 1998.

(51) Int. Cl.[7] .............................................. C12M 1/34
(52) U.S. Cl. .......................... 435/287.1; 435/288.7; 435/297.2; 435/309.2; 435/30; 422/62; 422/81; 436/52
(58) Field of Search ................................. 435/3, 30, 34, 435/39, 286.5, 287.1, 287.2, 287.3, 288.7, 297.2, 309.1, 309.2, 808; 436/52, 53, 164, 174, 179; 422/62, 81, 82, 82.05, 82.08, 99, 101, 103; 356/36

(56) References Cited

U.S. PATENT DOCUMENTS 3,018,224 A * 1/1962 Ferrari, Jr.
3,028,225 A * 4/1962 Sheen
3,674,672 A * 7/1972 Whitesell
4,025,393 A * 5/1977 Hirschfeld
4,242,447 A * 12/1980 Findl et al.
4,667,504 A * 5/1987 Hobson
4,845,025 A * 7/1989 Lary et al.
4,920,056 A * 4/1990 Dasgupta
5,055,198 A * 10/1991 Shettigar
5,330,914 A * 7/1994 Uhlen et al.
5,411,708 A * 5/1995 Moscetta

FOREIGN PATENT DOCUMENTS

JP     3-160980    * 7/1991
NL     7016218     * 5/1971

* cited by examiner

Primary Examiner—William H. Beisner
(74) Attorney, Agent, or Firm—Friederichs Law Firm PLC

(57) ABSTRACT

For direct and on-line study of the physiological states of cell cultures, a robust flow injection system has been designed and interfaced with flow cytometry (FI-FCM). The core of the flow injection system includes a microchamber designed for sample processing. The design of the microchamber allows not only an accurate on-line dilution but also on-line cell fixation, staining, and washing. The flow injection part of the system was tested by monitoring the optical density of a growing *E.coli* culture on-line using a spectrophotometer. The entire growth curve, from lag phase to stationary phase, was obtained with frequent sampling. The system is thus particularly useful since it operates automatically without direct operator supervision for extended time periods.

16 Claims, 7 Drawing Sheets

Figure 1:
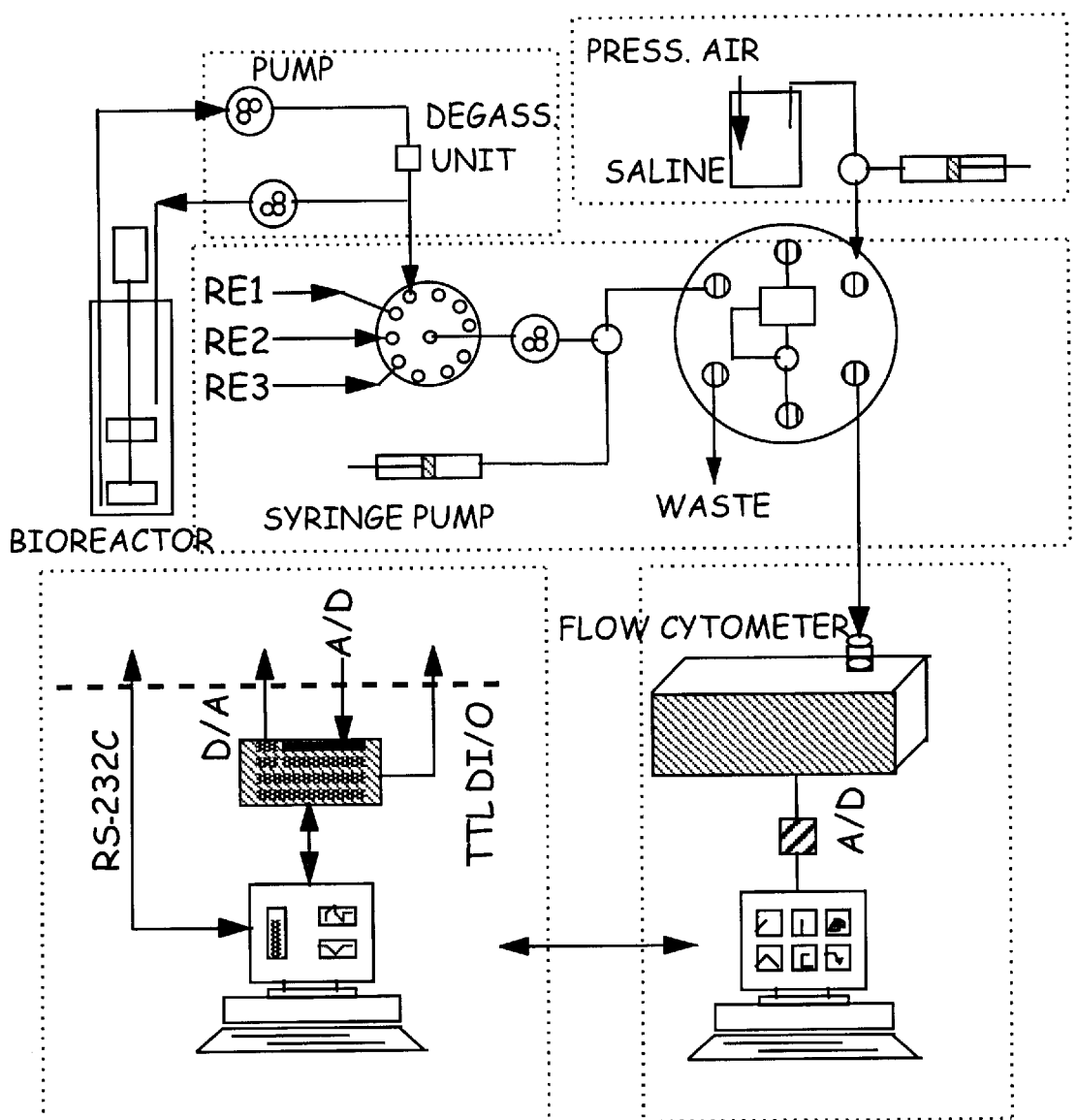

FLOW INJECTION FLOW CYTOMETRY SYSTEM FOR ON-LINE MONITORING OF BIROREACTORS AND METHOD FOR MONITORING

This application claims benefit of U.S. Provisional Patent application Ser. No. 60/079,970 filed on Mar. 30, 1998.

INTRODUCTION

There is ample evidence that growing cells are heterogeneous entities that differ from one another in their physiological states. Microbial heterogeneity may arise due to phenotypic changes associated with the cell cycle (Dien and Srienc, 1991, 1992), due to changes in the microenvironments of individual cells (Fowler and Dunlop, 1989, Dunlop and Ye, 1990), or due to mutations resulting in genotypic variations in the population (Hall, 1995). Thus, rates of growth associated parameters such as protein synthesis or substrate uptake are distributed in the population. From a biochemical engineering perspective, these population dynamics have profound implications since the overall productivity of the microbial process depends upon the contribution of each individual cell. One method to estimate such dynamics is by the use of flow cytometry.

In a process environment, rapid, repeated, and long term on line manual analysis is usually impractical, if not impossible. Therefore, a certain degree of automation is desirable, particularly for more complex analysis procedures such as flow cytometry. To date, a number of flow injection systems have been designed and widely used in microbial process control and automatic analysis (Ruzicka and Hansen, 1975, 1988; Reed, 1990; Munch et al., 1992), but most of them monitor population averaged properties. The concept of automatic flow cytometric analysis was introduced by Omann et al. (1985), who constructed a sample instruction devise fitted to a Becton Dickinson FACS cytometer. Kelley (1989) also developed a similar device. Pennings et al. (1987) developed a system based on continuous pumping cells and reagents with a peristaltic pump. Although the capabilities of these designs are rather limited, they are pioneering designs in automatic flow cytometry. Successful on line flow cytometry was demonstrated using a flow injection technique (Ruzicka, 1992).

The present invention provides for a flow injection system interfaced with a flow cytometer and a bioreactor to perform on line assessment of single cell property distributions. The versatility and performance of this system are demonstrated in several preliminary examples that show the utility of the system since it provides detailed quantitative information on growing cell populations that cannot be obtained with any other existing method.

Materials and Methods

Cell Strains, Growth Medium, Growth Conditions, and Staining Conditions

E. coli strain K12 was used in the growth experiment involving on line monitoring of optical density. Cells were grown in 300 mL 2XGYT complex medium (Sambrook, et al., s1989) in a 1 L flask placed in a 30° C. water bath and shaken at 225 rmp. The culture was aerated at 1 vvm by a peristaltic pump through an airstone (Cole Parmer, Vernon Hills, Ill.) immersed in the medium E.coli BL21 cells transformed with the plasmid pRSET/S65T (a kind gift from Dr. R. Y. Tsien, Howard Hughes Medical Center, San Diego) were used in the experiment to study the Gfp fluorophore formation kinetics and batch growth dynamics. The plasmid contains an ampicillin resistance marker gene, and the Gfp gene under the control of a T7RNA polymerase promoter. Cells were grown in LB complex medium containing ampicillin (100 µg/mL). Production of T7 RNA polymerase was regulated using an IPTG inducible lacZ promoter present in the host chromosome. IPTG (200 µg/mL) was used to induce Gfp expression, and chloramphenicol (30 µg/mL) was used to inhibit the protein synthesis when needed (Sambrook et al., 1989)

Saccharomyces cerevisiae strain YPH399a (MATa, ade2–101, leu2Δ1, lys2–80, his3Δ200, trplΔ63, ura3–52) cells were grown overnight on 3 mL YPD medium (Bacto yeast extract, 1% w/v, bacto peptone, 2% w/v, dextrose, 2% w/v) at 30° C. and 225 rpm in a 15 mL polystyrene test tube (Falxon). Cells were diluted to a concentration of ca. $1\times10^6$ cells in fresh medium, and the tube was placed on ice. Samples were automatically withdrawn into the microchamber of the flow injection system. Inside the microchamber, samples were washed with ice cold PBS, treated with chromatin denaturation solution (0,1 N HCl, 0.5% w/v Triton X-100, 1.75% w/v NaCl), washed with ice cold PBS, and strained with mithramycin A (Sigma, 30 µg/mL in PBS, 2mM $MgCl_2$). Fixation and denaturation steps were 2 minutes long, washes were 1 minute lone, and cells were tainted with mithramycin for 10 minutes. Fixation, denaturation, and washing were performed by continuously pumping the appropriate reagent through the microchamber while mixing the suspended cells using a magnetic stir-bar. A source of reagent is connected to a port of the microchamber such that reagent flows through this port and through the membrane and contact the sample on the sample handling side of the membrane.

FI-FCM System

The equipment used to construct the flow injection system is listed in Table 1. The components were interfaced to a personal computer using DT 2805 and DAS 1601 data acquisition and system control boards through DI/O and D/A subsystems. Labtech Notebook software (Laboratories Technology Corporation, Wilmington, Mass.) was used to control both boards. FIG. 1 shows a schematic overview of this FI-FCM system which consists of three subsystems: (i) sample delivery, (ii) sample handling, and (iii) sample injection and analysis.

A sample delivery loop transferred the cell culture from a bioreactor to the flow injection system. A static degassing unit was designed to release air bubbles trapped in the sample (FIG. 2a), and sample was continuously re circulated in this loop. During sampling periods, the cell culture with air bubbles was allowed to accumulate in the glass tube, and a weak vacuum was applied using a peristaltic pump. Due to a combination of static hydraulic buoyancy force and vacuum air bubbles were rapidly eliminated from the medium through a 0.45 µm inline filter. The degassed sample was then fed into the microchamber of the sample handling subsystem for further processing. The sample residence time in the delivery loop was minimized since the environmental conditions (in particular, the aeration) in the tubing are not the same as those in the bioreactor,. However, care was taken to avoid shear induced damage of the sample that might result from the use of very high flow rates in the tubing. Hence, Cole Parmer Masterflex silicon tubing (size #13, I.D. 0.75 mm) and a flow rate of 5 mL/min (0.19 m/sec) were used, resulting in a residence time of 10.5 sec.

The sample handling consists of a 10 position switching valve (#1, Table 1) connected with a precise peristaltic pump (#4 Table 1) to select up to 10 different streams, and a two way injection valve (#2 Table 1) incorporated with a microchamber to load and infect samples (FIG. 2b,c). The key component in sample handling is the microchamber which has been designed to allow on line sample dilution and staining (FIG. 2d). The unit essentially represents a stirred tank reactor with three ports that serve as inlets and outlets. Since dilution, staining processes, and other enzymatic reactions are basically mixing process, they can be easily carried out in the microchamber in a predictable manner.

Port A and B are directly connected to the microchamber, while Port C is connected to the microchamber through an inline filter. With this inline filter, fluids can flow through the microchamber freely but cells are retained inside. To load sample into the microchamber outlet C is blocked (FIG. 2d), sample is pumped through microchamber from port A to Port B. To perform on line dilution of cell samples, water is pumped through the microchamber from Port A to Port B at a predetermined flow rate F for a certain time t, such that the sample is diluted by a factor D given by $$D(t)=C(t)/C_0=e^{(F/V)t} \quad (1)$$

where V is the volume of the microchamber and $C_0$ is the initial cell concentration. In practice, the volume term is modified to account for the dead volume of the connection tubing. To perform on line staining port C is opened while port B is blocked. Solutions such as PBS, or ethanol are pumped through the microchamber from port A to port C, so that cells inside the microchamber can be washed, fixed and stained. After samples are so processed, they are injected into the flow cytometer for analysis.

The flow cytometer used was an Ortho Cytofluorograf IIs (Ortho Diagnostics Systems, Westwood, Mass.) equipped with an argon ion laser (Innova 90–5, Coherent Inc., Palo Alto, Calif.) and a Cicero data acquisition system (Cytomation, Fort Collins, Colo.). The laser was operated at 488 nm (Gfp) or 457 nm (mithramycin), and 100 mW beam power. A bandpass filter (525±15 nm) and an OG530 long-pass filter were used to collect Gfp and mithramycin fluorescences respectively. Data were acquired in listmode, pulse area, linear, and logarithmic configurations.

Results and Discussion

System Performance

To test the sample handling system a growth study of *E.coli* cells was carried out using a spectrophotometer as the detection device instead of a flow cytometer. The purpose of the experiment was to test the reliability of the sampling, degassing, and the dilution subsystems. A satisfactory performance of the system would yield the growth curve of a cell culture with frequent sampling points over the entire growth period by automatically carrying out dilutions to keep absorbance readings in the linear range when higher cell densities were reached.

Figure 3:
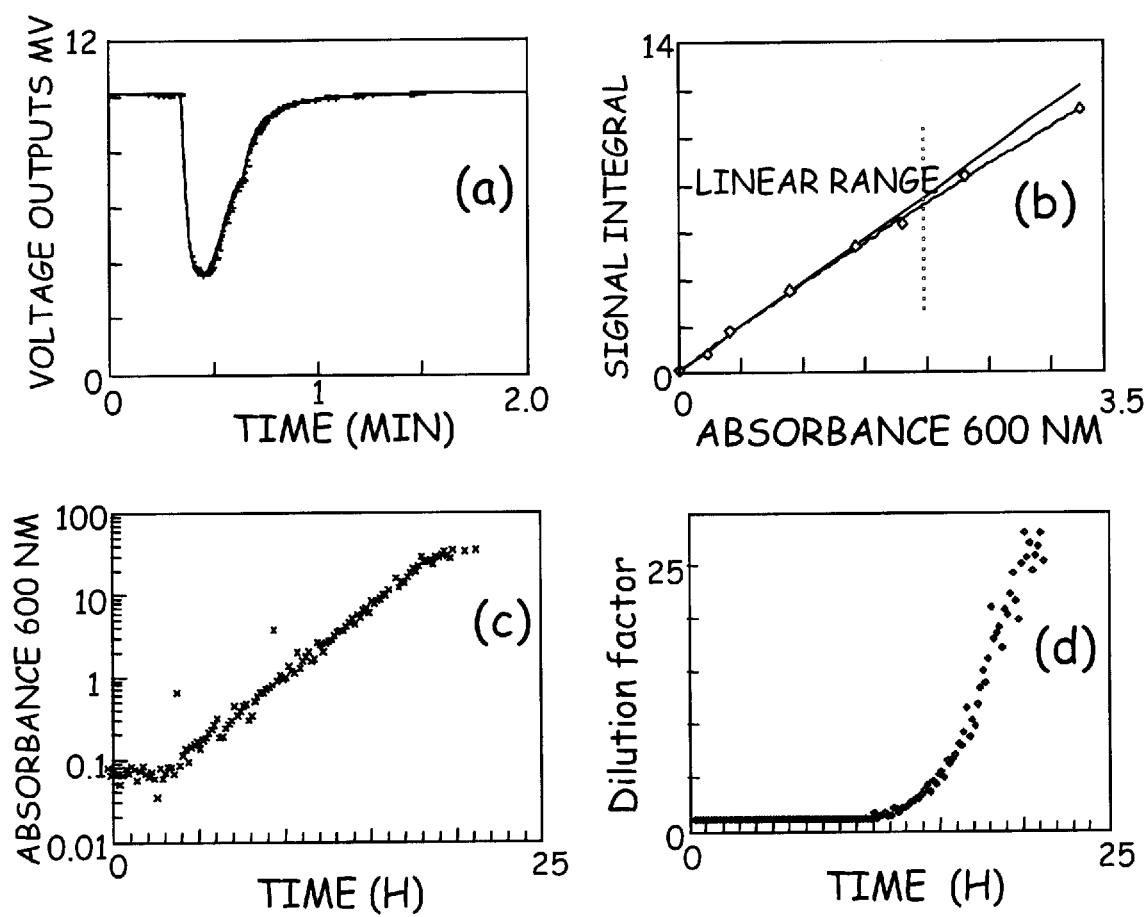

The output transmittance signals of the spectrophotometer were acquired using the A/D subsystem of DT2805 board. A typical output signal is shown in FIG. 3a. The signal resembles a gamma distribution due to the dispersion of the sample in the carrier stream. the sample concentration was determined by integrating over the entire duration of the signal pulse. Since the dispersion of the cell culture within the carrier stream is not linearly related with the sample concentration, the recorded transmittance signals are not directly proportional to the sample concentration. This relationship can be described by the Taylor dispersion (Taylor, 1953) as follows:

$$C(t) = \frac{M/\pi R^2}{\sqrt{4\pi Et}} e^{(z-vt)^2/4Et} \quad (2)$$

where C(t) is the concentration of the sample a the position of the detector at time t, M is the total amount of the sample injected into the carrier stream, E is the dispersion coefficient, R is the diameter of the tube, v is the velocity of the stream, and Z is the distance between the detector and the point of the injection. Transmittance is related to cell concentration according to Beer Lambert's law (Zubay, 1993), $$V(t)=10^{(1-KC(t))} \quad (3)$$

where V(t) is the transmittance output and K is extinction coefficient. Combing equations 2 and 3, the following expression can be derived to relate the amount of sample to the measured transmittance signal:

$$\int_0^\infty (1-\log V) dt \propto M \quad (4)$$

$$(1-\log V) dt \propto M \quad (4)$$

Equation 4 is valid over the same linear range described by Beer Lambert's law. This was determined to be the case for sample absorbances less than 2.0 (FIG. 3b). Therefore, on line dilutions were necessary for dense samples. A zero order algorithm was used to calculate the dilution factor for the next sample ($D_{j+k}$) based on the current concentration measurement ($C_i$) and the initial sample concentration ($C_0$). The algorithm $$D_{i+1}=C_i/C_0 \quad (5)$$

is valid when the frequency of sampling is greater than the frequency of cell division.

The lag phase, exponential growth phase, and the stationary phase can be clearly recognized in the growth curve thus obtained (FIG. 3c). On line measurements showed very few variations associated with measurement errors, and measurements were thus stable and consistent. The on line dilution started automatically 11 hours after the start of the growth experiment, and dilution factors increased from 1 to 27 over the span of the experiment (FIG. 3d). The degassing unit was able to efficiently remove air bubbles from the cell culture samples even during the late stages of the experiment when the cell culture was very dense (OD-40). The two abnormal points shown in FIG. 3a are probably due to air bubbles that likely have originated from open ports on the 10-Position Switching Valve. This potential problem can be avoided by sealing unused ports. One can note that the dilution factors calculated after the overshoots in the measurements did not diverge away, indicating that the zero order algorithm is stable for this application.

Reproducibility of the On-line Flow Cytometry Measurements

A stable sample stream is very important to obtain accurate measurements on a flow cytometer. Hence, pressurized air was used to drive sample from the microchamber to the flow cytometer (FIG. 2e). Most FI systems usually use a mechanical syringe pump. Using the syringe pump, it was found that the coefficient of variation of light scatter distributions of calibration beads obtained was higher than 10% with strong concomitant background noise. In contrast, the use of pressurized air to drive samples gave reproducible, noise free light scatter distributions of calibration beads.

To test whether the on-line measurements indeed yield the correct distributions, fly replicates of light scattering intensity distributions of S.cerevisiae cells measured on-line and off-line were compared (FIG. 4a). It can be seen that the distributions obtained from on-line measurements can be superimposed over those from off-line measurements. The Kolmogorov-Smirnov (K-S) statistic test (Neter, 1988) was performed to verify that the distributions can be considered statistically identical with a confidence level greater than 0.99. Thus, on-line measurements give the same information as off-line measurements.

Reproducibility of on-line measurements as a function of time was tested by comparing light scattering intensity distributions of uniform calibration beads (2.013±0.0251μm, Duke Scientific) measured every ten minutes over a span of 4 hours. Variance in light scattering distributions of these beads is a useful indicator of the optical alignment of the flow cytometer. Hence this measurement was used to estimate the stability of the on-line measurements. It was observed that the coefficient of variation (CV) of the distributions fluctuated very little over four hours of periodic sampling (FIG. 4b). A statistical analysis confirmed that the CVs were identical with 95% confidence (t test, Neter, 1988), confirming that the measurements and the instrument settings were not subject to a drift over time.

The flow rate of samples that can be applied in a flow cytometer depends upon the sample concentration. The arrival of cells of a given concentration at the analysis point in the flow cytometer is governed by Poisson statistics. Hence, sample concentrations have to be adjusted to ensure that the probability of 2 or more cells being analyzed simultaneously is minimized. Here, a threshold of 1% was set for coincident events, i.e., samples whose probability of coincidence of two or more cells exceeded 1% of the probability of single event occurrence were diluted prior to analysis. The lower end of sample concentrations was determined by the minimum number of events desired for acquisition and the time available for sample collection. In our system, the working range of sample concentrations resulted in event flow rates between 100 and 1000 events per second. To examine whether samples whose concentrations varied in this working range were processed similarly, their time profiles (i.e., number of events as a function of time) were analyzed after sample injected for a range of concentrations. Under ideal circumstances with no sample dispersion, these profiles would be described by exponentially decaying functions with the specific rate of decrease equal to the dilution rate of samples out of the mirochamber. The time profiles obtained experimentally were normalized to unit area to yield event frequency profiles for ease of comparison, and they were found to be identical (FIG. 4c). This observation has several important implications. First, the window between the time of injection of sample and the time of analysis of sample was independent of the actual sample concentration. Second, the relative cell number density of the same can be determined as the product of the number of events counted within a fixed time window (for e.g., the "sampling period", FIG. 4c) and the factor dilution. Third, the actual profiles obtained were compared to ideal profiles described above, and they were found to be very similar. After reaching a maximum less than 10 seconds after the sample front reaches the analysis point in the flow cytometer, event frequencies decreased as described by the ideal profile. This implies that the microchamber can indeed be approximated as an ideal stirred tank reactor. Finally, any residual sample is completely flushed away during the flushing period, and hence there is no cross contamination between successive samples. Thus, the system was robust in handling a range in cell concentrations, and yielded very reliable data.

Monitoring Cell Population Dynamics

Figure 5:
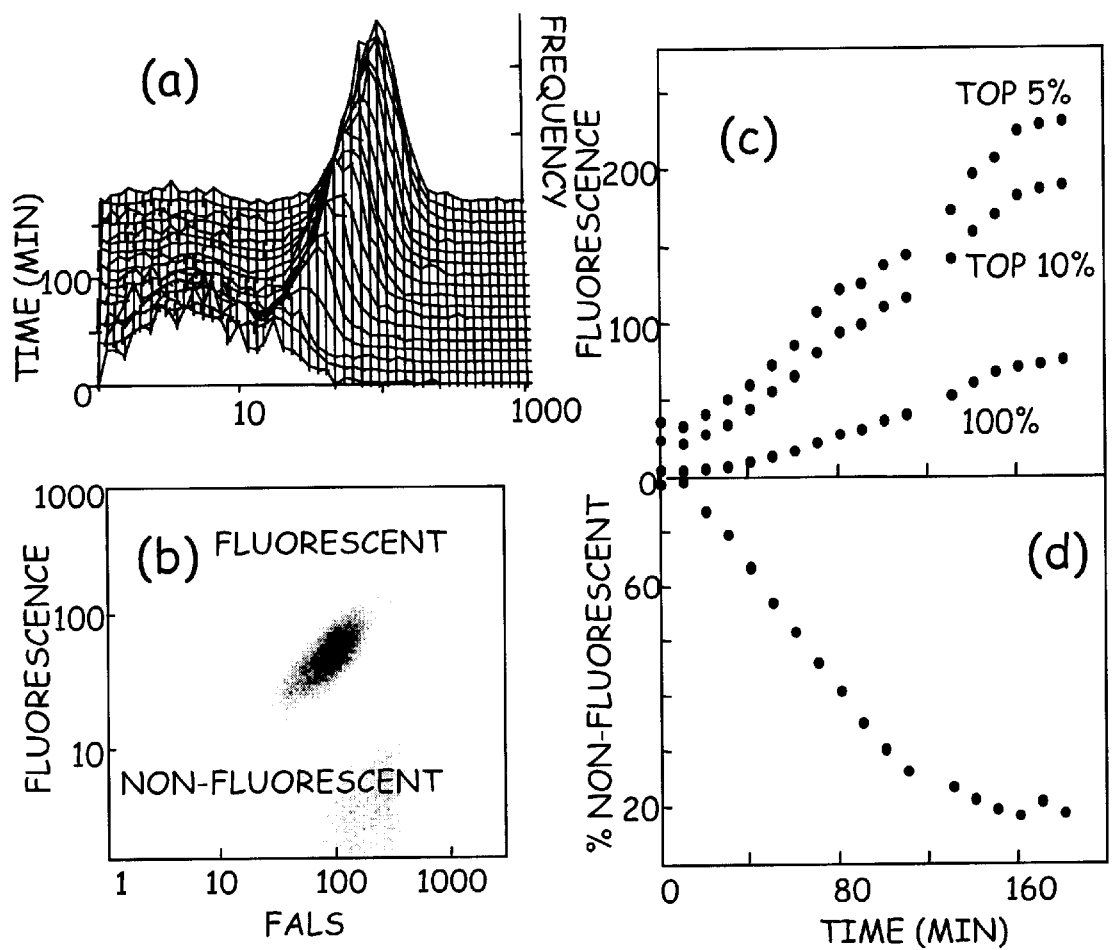

To simplify the process, we initially measured native properties of cells. These are usually restricted to light scatter intensity measurements. While these parameters are very useful in discriminating cell populations and, in some cases, in estimating cell viability, they usually cannot be directly related to intrinsic quantitative biological properties of cells. Hence, we have expressed the green fluorescent protein (Gfp) to obtain naturally fluorescent protein that has been expressed in many heterologous hosts (Cubitt et al., 1995), and is very useful reporter for quantitative, non invasive detection of single cell gene expression (Subramanian and Srienc, 1996, Natarajan et al., 1998). Gfp expression was induced by the addition of IPTG to exponentially growing E.coli cells. The objective of the experiment was to examine the heterogeneity in levels of protein expression in single cells in an exponentially growing population. Hence, protein synthesis was inhibited five minutes after induction by addition of chloramphenicol. Thus, expression of Gfp in all cells was restricted to a "pulse" of finite time. The time of induction is designated as time "0" in the graph shown (FIG. 5). The culture was sampled and analyzed every 10 minutes using on-line flow cytometry after induction and inhibition of protein synthesis. On-line dilution was not performed because inhibition of protein synthesis resulted in growth arrest and the cell concentration remained constant.

Shown in FIG. 5a is the time evolution of the cellular fluorescence distribution. The population was initially non fluorescent. After induction, the cells gradually increased in their fluorescence. The increase in the mean fluorescence value of the population (comparable to a population averaged assay) is shown in FIG. 5c ("100%"). The kinetics of increase in mean fluorescence are sigmoidal, possibly because nascent Gfp molecules have to fold, cyclize, and oxidize the fluorophore sequentially prior to turning fluorescent. The increase in fluorescence saturates approximately 3 hours post induction. however, a significant fraction of the population remains non fluorescent (20%, FIG. 5d). This subpopulation can be better visualized in the cytogram of FALS versus fluorescence (FIG. 5b). In addition, there is significant heterogeneity in expression among fluorescent cells, indicating variability in the capacity to produce heterologous protein in the population. From a biotechnological process perspective uniform maximal expression of protein is desirable among all cells in the population. One should note that this maximum expression level cannot be inferred from the mean of the entire heterogeneous population due to the presence of non producers and low-level producers. Rather, a single cell assay of the kind described here is necessary. In the above experiment, a choice of the top 10% or 5% of fluorescent cells indicated that this maximum capacity is 3- or 4-fold greater than the population average value (FIG. 5c).

Monitoring Batch Growth Dynamics of E.coli

In order to test the system over longer time periods, the FI-FCM system was used to monitor the growth dynamics of E.coli cells from lag phase to stationary phase. On-line dilution up to 700 fold was performed over the course of growth. E. coli BL21 cells transformed with plasmid pRSET/S65T were grown at 37° C. in complex medium containing ampicillin as a selection marker. Even though the culture was grown under non-inducing conditions, leaky expression of Gfp was observed in the population. The cell culture was sampled and analyzed every 10 minutes, and forward angle light scattering (FALS), right angle light scattering (RALS), and fluorescence intensity signals were collected.

After a short lag phase of ca. 20 minutes, cells grew exponentially for four hours, then entered stationary phase (FIG. 6a). The time evolution of the size (approximated by FALS intensity) distribution of growing E.coli culture from lag phase to stationary phase is shown (FIG. 6b). If growth of cells were balanced, then frequency distributions of various properties such as cell size or protein content would be expected to be time invariant. In the early exponential growth phase, the peak of the FALS distribution shifted to the right (including an increase in mean cell size), reached a maximum value, shifted back to lower mean intensity during late exponential growth. A similar trend is observed in the mean FALS signal intensity (FIG. 6d). Thus, growth was exponential, but not balanced. FALS intensity distribution of the growing culture was also monitored. Although Gfp synthesis was not induced, there was sufficient leaky expression of the protein for the fluorescence to be detectable. Interestingly, heterogeneity of expression was observed even among uninduced cells (FIG. 6c). Levels of leaky expression were seen to be inversely correlated to the growth phase as lag- and stationary-phase cells were more fluorescent than exponentially growing cells (FIG. 6d). Additionally, protein content distributions in the population also change with time during the exponential growth period, further indicating that growth was unbalanced as a time invariant physiological state is never reached.

Monitoring Cell Cycle Distribution of S.cerevisiae

To demonstrate the staining capability of FI-FCM system, DNA content of S.cerevisiae cells were measured on-line as described in Methods. Even the application of a simple, single stain requires multiple preparatory steps during which cell samples might potentially be lost. To eliminate this possibility, a 0.2 $\mu$m inline filter was used to retain cells while they were treated with various chemicals. The flow through port C was analyzed for presence of cells after each step to ensure the integrity of the membrane. Membrane clogging, frequently a problem in many membrane systems, was virtually eliminated in our design because of co-existing tangential flow between ports A and B, continuous vigorous stirring in the mircochamber, and dilution of cells to a concentration of ca. $10^5$ per mL prior to initiation of staining. Vigorous stirring also ensured that cells did not clump together during the fixation step.

In order to demonstrate staining capability, replicates of a sample of S.cerevisiae cells in late exponential phase were washed, fixed, treated with chromatin denaturation solution, stained with mithramycin (MI), and analyzed on the FCM. An asynchronous population would be expected to have a bimodal DNA distribution, where the two modes correspond to cells in the G1 phase (FIG. 7c). DNA distributions obtained were compared with autofluorescence measurements on fixed and denatured cells that had not been stained. Autofluorescence distribution is clearly unimodal, and well separated from the stained distributions (FIG. 7c). IN comparison, staining does not affect light scatter intensity measurements, hence FALS distributions of unstained and stained cells are identical (FIG. 7a). DNA distributions for three replicate samples were also found to be statistically identical, ensuring reproducibility of the staining process (K-S test, Neter, 1988). Since the entire process is automated, it is easy to envision the use of more complicated staining protocols to tag and quantitate other cellular components also.

Discussion

To determine the state of a growing cell culture, conventional monitoring systems typically evaluate measurable quantities of the abiotic phase from which the state of the culture is inferred. Direct measurement of the physiological state is usually not possible because quantitative methods to rapidly assay the composition of the biomass are limited. Furthermore, the properties of individual cells are different and distributed over a range of physiological states. Therefore, population average data provide only limited information, and accurate information must be sought at the single cell level.

Fredrickson and co workers (1967, 1968) proposed a general mathematical framework, known as population balance theory, to describe cell growth and its interaction with the environment (see also Ramkrishna, 1979, 1985). In this theory, the state of individual cells is specified by the physiological state vector, a collection of state properties such as cell size, protein content, or DNA content. The resulting population balance equations essentially are number balances on individual cells of a population, which keep track of, not only the generation and disappearance of cells, but also of the continuous change in the identity of cells due to physiological growth processes. This modeling framework (known as corpuscular and structured) most realistically represents the evolution of a heterogeneous microbial population. Versions of this model have been used to extract growth parameters from single cell property distributions obtained using flow cytometry (Dien and Srienc, 1991, Kromenaker and Srienc, 1991, 1994 a,b,c). These analyses were however performed off-line for special cases. In general, it has been difficult to apply the population balance model to real microbial processes due to lack of experimental data that would permit identification of model parameters. Such data could possibly be generated by flow cytometry interfaced with appropriate instrumentation for on-line sample processing and analysis.

Hence, we designed and constructed a versatile and modular flow injection flow cytometry (FI-FCM) system. To display the detail of information that can be obtained, the system was used to monitor the heterogeneity of protein expression in an E.coli cell population. The results clearly reveal the need for single cell analysis, since cellular content of even a single component such as Gfp content was distributed in the population. Frequent, automated sampling permitted observation of smooth trends of cellular phenomena. This data could be used to generate accurate estimates of the kinetics of transient events. Furthermore, it has been shown that the system can be used to monitor long term fermentation processes during the course of which cell concentrations would change significantly. Since the system does not require any operator intervention, it is particularly suitable for process monitoring and control applications. The data obtained can be used to determine the detailed physiological state of distribution of the cell population. Additionally, single cell growth parameters can be evaluated. In order to better define the composition of single cells, the range of cellular components that can be monitored can be explained by taking advantage of the design of our microchamber, which permits on-line cell fixation, and staining, as demonstrated in this work.

The presented examples demonstrate that the developed system represents a powerful tool to study cell physiology in a detail that was previously not possible. Moreover, the FI-FCM system will be advantageous for monitoring bioreactors in studies involving transient growth phenomena, estimation of cellular kinetics, or study of synchronous or cyclic trends that might not be observed with infrequent sampling. The system thus has significant potential in biotechnology for the monitoring of microbial populations without the need for excessive manual intervention.

TABLE 1

List of Equipment

| Equipment | Manufacturer | Control Method |
|---|---|---|
| 1 10-position switching valve, Model C25Z | Valco Instruments Co. Inc., Houston, TX | TTL output, DI/O port #1, DT2805 |
| 2 Two-way injection valve, Model C22Z | Valco Instruments Co. Inc., Houston, TX | TTL output, DI/O port #1, DT2805 |
| 3 Three-way switching valve, Model 01367-72 | Cole-Partner, Vernon Hills, IL | Relay driven, DI/O port #0, DT2805 |
| 4 Peristaltic Pump, 7520-50 | Cole-Partner, Vernon Hills, IL | Current output, D/A port #1, DT2805 Board |
| 5 Syringe Pump, Pump22 | Harvard Instrumentation, Harvard, MA | RS-232c |
| 6 Peristaltic Pump, 7520-20, 7520-30 | Cole-Partner, Vernon Hills, IL | Masterflex speed control unit |
| 7 Magnetic Stir Plate, Model 120s | Fisher Scientific, Pittsburgh, PA | |
| 8 LH fermentor, 2 liter | LH Fermentation, Hayward, CA | LH fermentor control unit |
| 9 DT2805 data acquisition and system control board | Data Translation, Marlboro, MA | |
| 10 DAS1601 data acquisition and system control board | Keithley Data Acquisition, Taunton, MA | |
| 11 Computer, Vectra/66 | Hewlett Packward, | Interfaced with flow cytometer |
| 12 Computer, 486/25c | Gateway2000, N. Sioux City, SD | Interfaced with FI system |

FIGURE LEGENDS

FIG. 1 An overview of FI-FCM system. The flow injection system consists of three parts: Sample Delivery, Sample Handling, and Sample Injection. Sample from a bioreactor is first brought to a multiposition valve and degassing is performed. Up to 10 different samples or reagents can be selected and pumped into the system using the multiposition valve connected with a precise peristaltic pump. A microchamber connected to a two way injection valve is used to dilute samples or mix sample with different reagents. After treatment, samples are carried to the flow cytometer in a pulse free manner by the mobile phase which is driven by pressurized air. The flow injection system is controlled by a PC through two data acquisition and system control boards. Flow cytometric data acquisition and analysis are performed by another PC.

Figure 2:
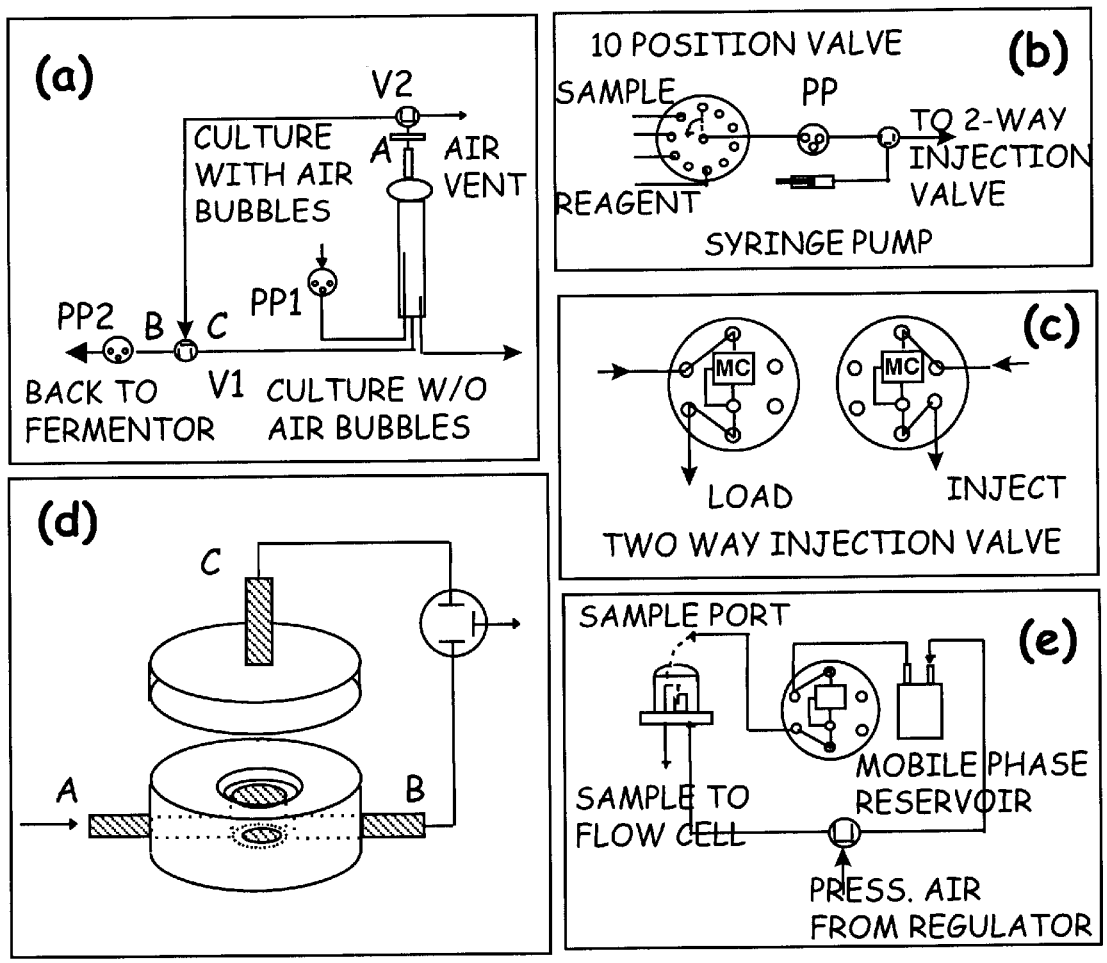

FIG. 2 (a) The static degassing unit. Air bubbles trapped in the cell culture escape from the medium due to the buoyancy force enhanced by the weak vacuum provided by a peristaltic pump (PP2). 2(b), 2(c) Schematic of Sample Handling subsystem. The center line of the 10-position switching valve is connected to a peristaltic pump (PP). Up to 10 different streams can be fed into the system using this pump. The syringe pump (SP) is specifically assigned to perform on-line dilution. A mircochamber is connected in the two way injection valve. 2(d) Mircochamber. Two side connections (A, B) allow fluids and cell particles to flow through and the vertical connection (C) is separated from the microchamber through a membrane which allows only fluids to pass through. 2(e) Sample injection subsystem.

FIGS. 3(a)–3(d) E.coli Growth curve. E.coli BL21 cells were grown in 2XGYT medium at 30° C., and the optical density of the cell culture was monitored on-line every 10 minutes for 22 hours. The doubling time was estimated at 2.31 hours. 3(b) On line dilution. On line dilution started automatically 11 hours after the start of the experiment and the dilution factor increased to 27 over the course of the experiment.

Figure 4:
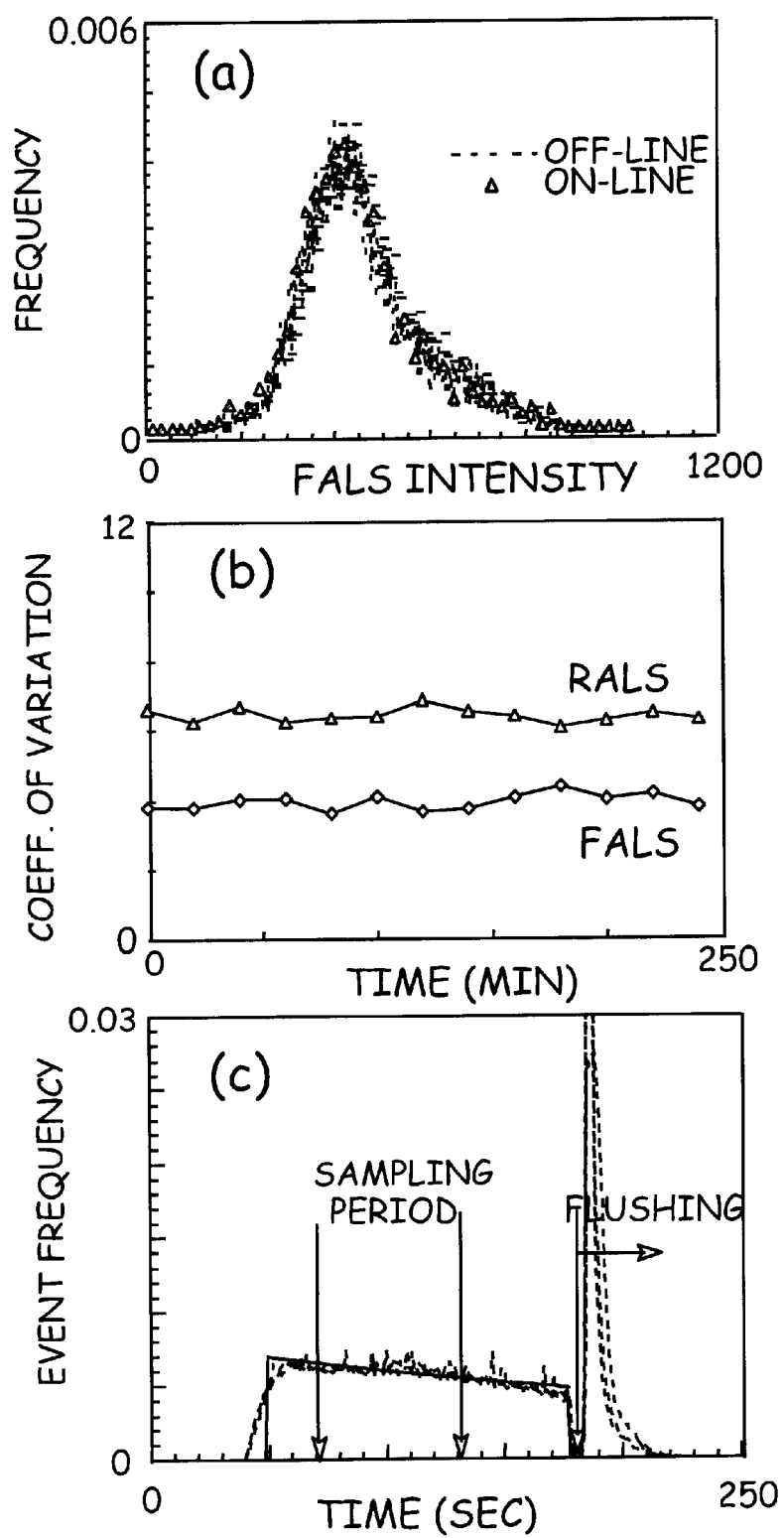

FIG. 4 (a) Reliability. The light scatter distributions of on-line and off-line measurements are compared to test the reliability of the on-line measurements. 4(b) Reproducibility. The coefficient of variation of light scatter distributions of uniform calibration beads were measured over an extended time period to test the reproducibility of the on-line measurements. 4(c) Robustness. The time profiles of event frequencies of samples of various concentrations (400, 700 and 1700 events/sec, - - - ) were compared with an ideal profile that would be obtained in the absence of sample dispersion (_). The "sampling period" (time window when samples are acquired) and "flushing period" of the sample analysis cycle are indicated.

FIG. 5(a) The time evolution of the fluorescent populations. 5(b) The fluorescent population heterogeneity. A distinct population of non fluorescent cells were observed. 5(c) The specific rate of increase of fluorescence of the top 5% and 10% fluorescent fractions is greater than the mean specific rate of the entire population. 5(d) The fraction of non-fluorescent cells was determined by comparing fluorescence intensity distributions of samples with those obtained from E.coli BL21 cells not expressing Gfp (negative control). The fraction decreased to a final value of ca. 20%. This population represents plasmid free cells.

Figure 6:
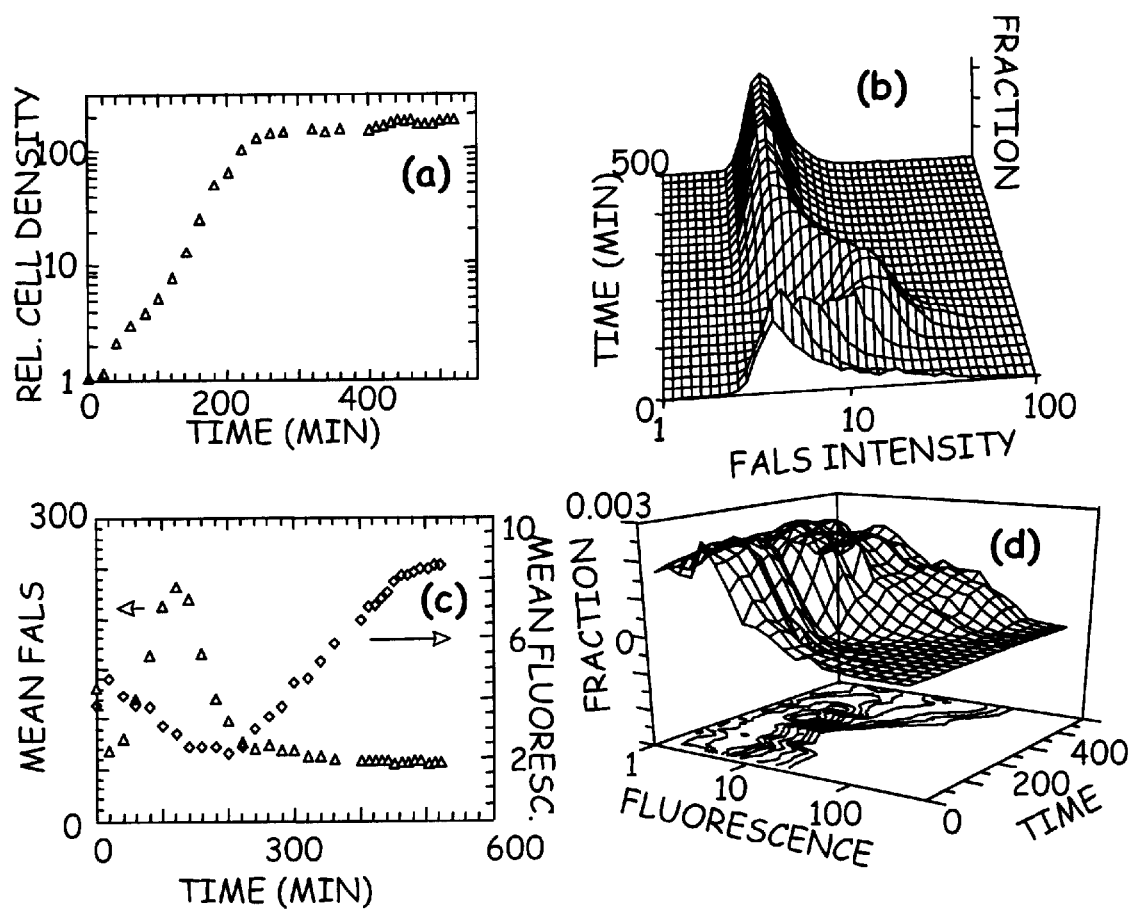

FIG. 6 (a) The growth curve. The relative number density of the sample was measured by counting the number of cells analyzed during the sampling period and by setting the number density of the first sample as 1. 6(b) The size distribution of growing E. coli culture. The forward angle light scatter intensity was collected every 10 minutes to characterize the size distribution. 6(c) Mean intensities of light scatter (correlated with cell size) and fluorescence of the population changed over the course of cell growth. During exponential growth, cell size increased while protein content decreased. The reverse trend was observed in the stationary phase. 6(d) The time evolution of the fluorescence intensity distributions. The majority of the cells were non fluorescent during exponential growth. Cells became increasingly more fluorescent during late exponential/stationary phase, until, at the end of the experiment, two populations could be distinguished.

Figure 7:
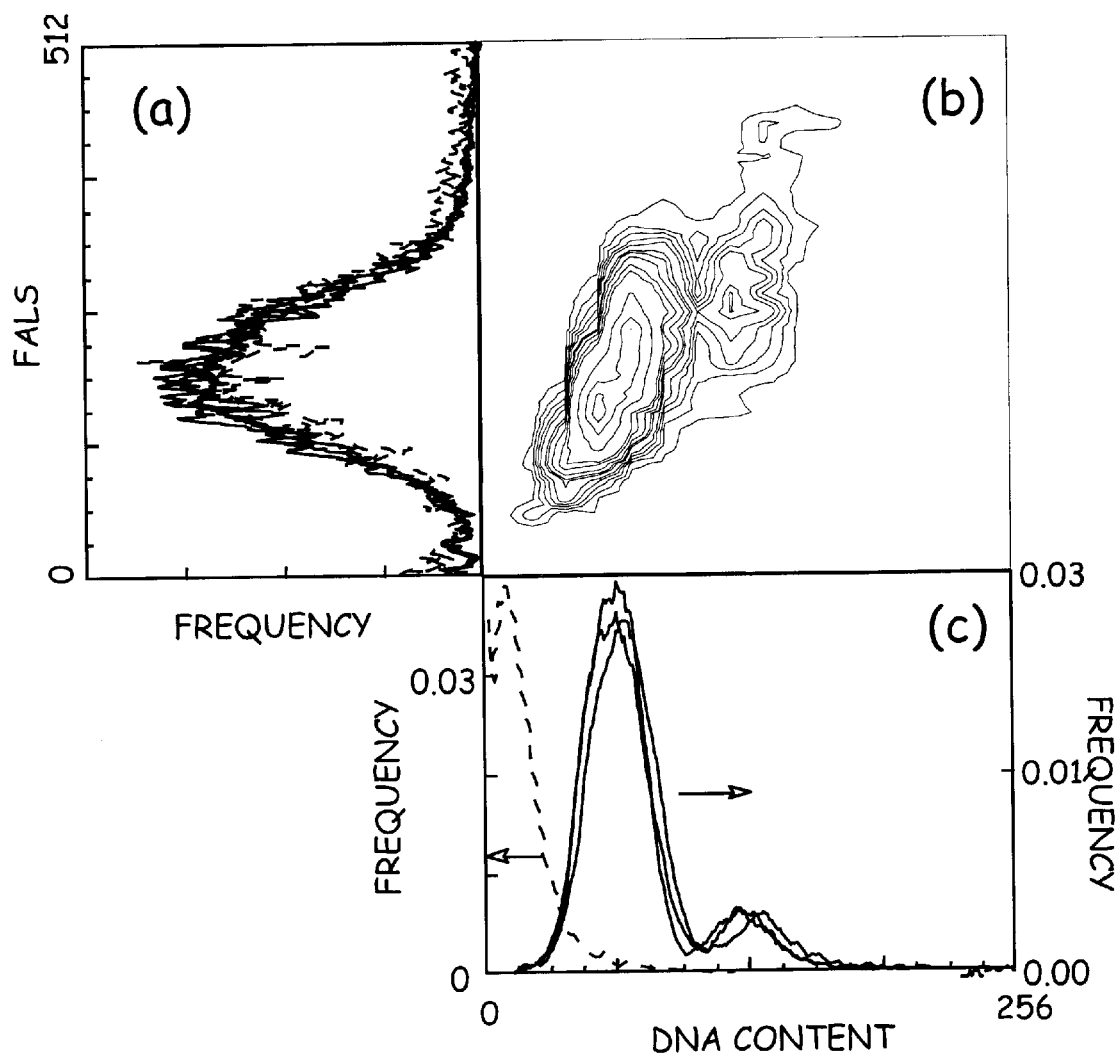

FIG. 7 (b) A bivariate histogram of DNA content and forward angle light scatter intensity (FALS) of a late exponential s.cerevisiae culture. The two sub populations observed correspond to cells in the G1 and G2 cell cycle phases. 7(c) DNA content distribution of three replicate samples of S.cerevisiae cells (—,Y2 axis) are compared with autofluorescence measurements of a fixed but unstained population (---,Y1 axis). DNA distributions were obtained by staining with MI as described in the Methods. All distributions are normalized to unit area for ease of comparison. Autofluorescence distribution is clearly unimodal, and well separated from DNA distributions. 7(a) However, staining does not affect light scatter intensity measurements, and FALS distributions of stained and unstained S.cerevisiae cells are identical. Univariate data was collected over 1024 channels, and binned into 128 channels for display in bivariate histogram.

As used herein, the following terms are given the associated meanings:

A "substrate" refers to a compound capable of interaction with a biological sample, such as by attaching to a portion of the biological sample or otherwise changing the chemical nature of the biological sample, which can aid in detection of the biological sample. Such substrates can include isotopic labels, stains, enzymes, and the like, which are typically in the form of an aqueous solution thereof.

A "semi-permeable membrane" refers to a microporous structure, either nature of synthetic, which acts as a filter in the range of molecular dimensions, allowing for the passage of ions, solvents (including water), and relatively small molecules, but are substantially impermeable to relatively large particles, such as virus and individual cells. Preferably, semi-permeable membranes are porous having a pore size in the range of about 0.1 micrometers to about 0.5 micrometers.

A "nucleic acid fragment" refers to a sequence of nucleotide monomers that forms DNA or FNA composed of a nitrogenous base bounded to a sugar (ribose or deoxyribose) bonded to a phosphate.

A "polypeptide" refers to a naturally occurring or synthetic (recombinant or chemical) molecule essentially composed of amino acids, typically linked together by their amino and carboxy groups and can be categorized by structural size, complexity, and biological properties, which may include a hormone, a neurotransmitter, a growth factor, or an enzyme, to name a few.

An "organelle" refers to a portion of a cell having a specific function, distinctive chemical constituents, and characteristic morphology and is considered to be a subsystem of the cell. Examples include a mitochondria, a chloroplast, a nucleus, an endoplasmic reticulum, a peroxisome, a glyoxisome, and the like.

A "prokaryotic cell" refers to a single cell organism in which the genome DNA is not enclosed in a separate organelle (e.g., nucleus).

A "eukaryotic cell" refers to an organism in which the genomic DNA is enclosed in a separate organelle (e.g., nucleus), wherein the genomic DNA is generally organized as chromosome(s).

A "virus" refers to an agent naturally able to infect a host cell and bearing a nucleic acid fragment allowing its complete reproduction within a specific host cell.

A "fluorescent label" refers to an agent that are typically a dye compound that emits visible radiation in passing from a higher to a lower electronic state, and can include such compounds as fluorescein, rhodamine, and the like.

An "isotopic label" refers to those compounds that are beta, gamma, and even alpha emitters, and can include such elements as P32, S35, I125, and the like.

An "enzymatic label" refers to a compound that reacts with a substrate in which the substrate undergoes a detectable chemical change, such as a color change, and can include such enzymes as horse radish peroxidase, luciferase, and the like.

A "stain" refers to a colorant that is capable of attaching to a biological sample, typically irreversibly, and can include such conventional colorants as coomassie blue and the like.

A "fixed biological sample" refers to a preserved specimen so that a substantial portion of the specimen's features are preserved as it was when alive. Typical agents used in fixing biological samples include dilute acids, alcohols, and coagulants.

What is claimed is:

1. A device for monitoring a biological factor comprising:
   a microchamber including a sample handling portion, a substrate handling portion, and a semi permeable membrane, said sample handling portion being in communication with said substrate handling portion through said semi-permeable membrane, said semi-permeable membrane being permeable to relatively small molecules and not permeable to relatively large molecules;
   said device further including a sample delivery loop, an analysis delivery conduit and a substrate delivery conduit, said sample handling portion being in fluid communication with both said sample delivery loop and said analysis delivery conduit;
   said substrate handling portion being in fluid communication with said substrate delivery conduit; and
   said device further including means for measuring properties of said large molecules, said means for measuring being in communication with said sample handling portion through said analysis delivery conduit.

2. The device of claim 1 further comprising a bioreactor in communication with the sample handling portion of the microchamber through the sample delivery loop.

3. The device of claim 1 wherein the semi-permeable membrane comprises of porous membrane capable of retaining a biological material suspension sample on the sample handling portion of the microchamber while allowing a substrate solution to cross back and forth across the semi-permeable membrane from the substrate handling portion to the sample handling portion.

4. The device of claim 3 wherein the biological suspension comprises a detectable portion of an organism selected from the group of a virus, a prokaryotic cell, an eukaryotic cell, and a mixture thereof.

5. The device of claim 1 wherein the semi-permeable membrane comprises a porous membrane having pores within a size range of about 0.1 micrometers to about 0.5 micrometers.

6. The device of claim 1 further comprising a pressurized air line in communication with the analysis delivery conduit.

7. The device of claim 1 wherein a tangential flow exists between the sample delivery loop and the analysis delivery conduit in the sample handling portion of the microchamber.

8. The device of claim 1 wherein the substrate delivery conduit is in operative communication with a substrate solution reservoir, wherein the substrate solution comprises an indicator selected from the group consisting of a fluorescent label, an isotorpic label, and enzymatic label, and a colorant.

9. The device of claim 1 wherein said semi permeable membrane has pores in the range of about 0.1 to 0.5 micrometers.

10. The device of claim 9 wherein said means for measuring comprises a flow cytometer in communication with said sample handling portion of the microchamber through the analysis delivery conduit.

11. A method for direct monitoring a physiological state comprising the steps of:
    introducing a biological sample comprising a relatively small molecule portion and a relatively large molecule biological portion into a sample handling portion of a microchamber;
    introducing a substrate into a substrate handling portion of the microchamber;
    allowing the substrate to cross a semi permeable membrane that separates the sample handling portion of the microchamber and the substrate handling portion of the microchamber to separate said small molecule portion and said large molecule biological portion so that a treated biological sample is formed; and delivering the treated biological sample to a flow cytometer for analysis.

12. The method of claim 11 further comprising analyzing the treated biological sample to determine a physiological state of the biological sample.

13. The method of claim 11 wherein the method is automated.

14. The method of claim 11 wherein the step of delivering the treated biological sample to a flow cytometer for analysis comprises applying pulse-free pressurized air to introduce the treated biological sample into the flow cytometer.

15. The method of claim 11 wherein the treated biological sample is selected from the group consisting of a fixed sample, a stained sample, an isotopic labeled sample, a fluorescently labeled sample, an enzymatically sample, and a mixture thereof.

16. The method of claim 11 wherein the biologic sample is selected from the group consisting of a virus, a prokaryotic cell, a eukaryotic cell, a nucleic acid fragment, a polypeptide, an organelle, and a mixture thereof.

* * * * *